United States Patent [19]
Allen et al.

[11] Patent Number: 5,837,546
[45] Date of Patent: *Nov. 17, 1998

[54] ELECTRONIC ASSAY DEVICE AND METHOD

[75] Inventors: Michael P. Allen, Los Gatos; Joel M. Blatt, Palo Alto; Joseph T. Widunas, Fremont, all of Calif.

[73] Assignee: Metrika, Inc., Sunnyvale, Calif.

[*] Notice: The term of this patent shall not extend beyond the expiration date of Pat. No. 5,580,794.

[21] Appl. No.: 657,894

[22] Filed: Jun. 7, 1996

Related U.S. Application Data

[63] Continuation-in-part of Ser. No. 455,236, May 31, 1995, Pat. No. 5,580,794, which is a continuation of Ser. No. 111,347, Aug. 24, 1993, abandoned.

[51] Int. Cl.⁶ .................................................. G01N 21/78
[52] U.S. Cl. .................... 436/169; 422/58; 422/82.05; 422/82.09
[58] Field of Search ............................ 422/56, 58, 82.05, 422/82.08, 82.09; 364/497, 499; 436/169, 170

[56] References Cited

U.S. PATENT DOCUMENTS

| | | | |
|---|---|---|---|
| D. 282,644 | 2/1986 | Collister | D10/46 |
| D. 292,277 | 10/1987 | Collister | D10/46 |
| D. 294,807 | 3/1988 | Stiso | D10/81 |
| D. 318,331 | 7/1991 | Phillips et al. | D24/169 |
| D. 318,811 | 8/1991 | Caruso | D24/169 |
| D. 323,893 | 2/1992 | Arioka | D24/169 |
| D. 334,065 | 3/1993 | Collister | D24/232 |

(List continued on next page.)

FOREIGN PATENT DOCUMENTS

| | | |
|---|---|---|
| 2019865 | 6/1990 | Canada . |
| 2020029 | 6/1990 | Canada . |
| 2028968 | 10/1990 | Canada . |
| 0125118 | 11/1984 | European Pat. Off. . |
| 0182647 | 5/1986 | European Pat. Off. . |
| 0217403 | 4/1987 | European Pat. Off. . |
| 0284232 | 9/1988 | European Pat. Off. . |

(List continued on next page.)

OTHER PUBLICATIONS

A Dot–Immunobinding Assay for Monoclonal and Other Antibodies, Richard Hawkes, Evelyn Niday, and Julian Gordon, Analytical Biochemistry 119, pp. 142–147 (1982).
Detection of Specific Hybridoma Clones by Replica Immunoadsorption of Their Secreted Antibodies, Jacqueline Sharon, Sherie L. Morrison, and Elvin A. Kabat, Dec. 7, 1978, Proc. Natl. Acad. Sci. USA vol. 76, No. 3, pp. 1420–1424 Mar. 1979.

(List continued on next page.)

*Primary Examiner*—Maureen M. Wallenhorst
*Attorney, Agent, or Firm*—Timothy H. Gens; Trial & Technology Law Group

[57] ABSTRACT

The present invention provides an assay device for determining the presence of one or more selected analytes in a sample. The device includes a housing having an exterior surface and defining an interior area. A sample receptor receives the sample. A sample treatment strip reacts the sample with a reagent to yield a physically detectable change which correlates with the amount of selected analyte in the sample. A detector responds to the physically detectable change and produces an electrical signal which correlates to the amount of the selected analyte in the sample. A processor converts the electrical signal to a digital output. A starter automatically activates the processor and detector upon the application of the sample to the device. A display visually displays the digital output external to the housing and is connected to the processor. The present invention also provides a method for determining the presence of one or more selected analytes in a sample within a disposable housing, automatically starting a diagnostic device to analyze a sample, and displaying quantitative assay results for a plurality of selected analytes in a sample on a diagnostic device.

29 Claims, 9 Drawing Sheets

U.S. PATENT DOCUMENTS

| | | | |
|---|---|---|---|
| 4,038,485 | 7/1977 | Johnston et al. | 435/4 |
| 4,094,647 | 6/1978 | Deutsch et al. | 435/4 |
| 4,129,417 | 12/1978 | White | 436/169 |
| 4,160,008 | 7/1979 | Fenocketti et al. | 422/56 |
| 4,168,146 | 9/1979 | Grubb et al. | 435/7.92 |
| 4,235,601 | 11/1980 | Deutsch et al. | 436/514 |
| 4,275,149 | 6/1981 | Litman et al. | 435/7.91 |
| 4,281,061 | 7/1981 | Zuk et al. | 435/188 |
| 4,302,536 | 11/1981 | Longnecker | 435/7.25 |
| 4,313,734 | 2/1982 | Leuvering | 436/525 |
| 4,361,537 | 11/1982 | Deutsch et al. | 422/56 |
| 4,366,241 | 12/1982 | Tom et al. | 435/7.91 |
| 4,373,932 | 2/1983 | Gribnau | 436/501 |
| 4,376,110 | 3/1983 | David et al. | 436/513 |
| 4,435,504 | 3/1984 | Zuk et al. | 435/7.91 |
| 4,446,232 | 5/1984 | Liotta | 435/7.93 |
| 4,517,288 | 5/1985 | Giegel et al. | 435/5 |
| 4,518,259 | 5/1985 | Ward | 356/446 |
| 4,552,458 | 11/1985 | Lowne | 356/446 |
| 4,552,839 | 11/1985 | Gould et al. | 455/7 |
| 4,627,445 | 12/1986 | Garcia et al. | 128/770 |
| 4,637,403 | 1/1987 | Garcia et al. | 128/770 |
| 4,637,978 | 1/1987 | Dappen | 435/11 |
| 4,654,310 | 3/1987 | Ly | 436/164 |
| 4,703,017 | 10/1987 | Campbell et al. | 436/501 |
| 4,731,726 | 3/1988 | Allen, III | 364/416 |
| 4,734,360 | 3/1988 | Phillips | 435/25 |
| 4,740,468 | 4/1988 | Weng et al. | 435/7.91 |
| 4,774,192 | 9/1988 | Terminiello | 436/530 |
| 4,787,398 | 11/1988 | Garcia et al. | 128/770 |
| 4,791,461 | 12/1988 | Kishimoto | 356/446 |
| 4,806,312 | 2/1989 | Greenquist | 422/56 |
| 4,853,335 | 8/1989 | Olsen et al. | 436/527 |
| 4,855,240 | 8/1989 | Rosenstein et al. | 436/514 |
| 4,857,453 | 8/1989 | Ullman et al. | 435/7.92 |
| 4,861,711 | 8/1989 | Friesen | 436/7 |
| 4,868,108 | 9/1989 | Bahar | 435/7.92 |
| 4,923,800 | 5/1990 | Ly | 435/10 |
| 4,927,769 | 5/1990 | Chang et al. | 436/518 |
| 4,935,346 | 6/1990 | Phillips | 435/14 |
| 4,943,522 | 7/1990 | Eisinger et al. | 435/7.25 |
| 4,943,525 | 7/1990 | Dawson | 435/5 |
| 4,959,307 | 9/1990 | Olson | 435/7.91 |
| 4,959,324 | 9/1990 | Ramel et al. | 436/169 |
| 4,960,691 | 10/1990 | Gordon et al. | 435/6 |
| 4,973,549 | 11/1990 | Khanna et al. | 435/11 |
| 4,981,786 | 1/1991 | Dafforn et al. | 435/7.92 |
| 4,995,402 | 2/1991 | Smith et al. | 436/524 |
| 4,999,285 | 3/1991 | Stiso | 435/7.9 |
| 4,999,287 | 3/1991 | Allen et al. | 435/11 |
| 5,004,583 | 4/1991 | Guruswam | 422/58 |
| 5,029,583 | 7/1991 | Meserol | 128/633 |
| 5,035,704 | 7/1991 | Lambert | 606/182 |
| 5,036,000 | 7/1991 | Palmer et al. | 435/26 |
| 5,037,614 | 8/1991 | Makita et al. | 422/68.1 |
| 5,039,607 | 8/1991 | Skold et al. | 435/7.5 |
| 5,049,487 | 9/1991 | Phillips et al. | 435/4 |
| 5,059,394 | 10/1991 | Phillips | 422/68.1 |
| 5,064,618 | 11/1991 | Baker | 422/82.01 |
| 5,073,484 | 12/1991 | Swanson et al. | 435/7.92 |
| 5,075,078 | 12/1991 | Osikowicz et al. | 422/56 |
| 5,079,174 | 1/1992 | Buck et al. | 436/538 |
| 5,087,556 | 2/1992 | Ertinghausen | 435/7.9 |
| 5,091,153 | 2/1992 | Bachand | 422/58 |
| 5,096,669 | 3/1992 | Lauks | 422/61 |
| 5,096,837 | 3/1992 | Fan et al. | 436/514 |
| 5,104,619 | 4/1992 | Castro | 422/56 |
| 5,114,350 | 5/1992 | Hewett | 435/286.4 |
| 5,114,859 | 5/1992 | Kagenow | 436/50 |
| 5,120,643 | 6/1992 | Ching | 435/7.92 |
| 5,126,247 | 6/1992 | Palmer | 435/25 |
| 5,126,276 | 6/1992 | Fish | 436/531 |
| 5,132,086 | 7/1992 | Allen et al. | 422/56 |
| 5,135,716 | 8/1992 | Thakore | 422/56 |
| 5,141,850 | 8/1992 | Cole et al. | 436/525 |
| 5,141,875 | 8/1992 | Kelton et al. | 436/514 |
| 5,145,645 | 9/1992 | Zakin | 436/525 |
| 5,149,622 | 9/1992 | Brown | 435/5 |
| 5,155,025 | 10/1992 | Allen et al. | 435/11 |
| 5,164,294 | 11/1992 | Skold et al. | 435/7.5 |
| 5,168,042 | 12/1992 | Ly | 435/7.1 |
| 5,171,688 | 12/1992 | Hewett et al. | 435/287.8 |
| 5,173,433 | 12/1992 | Bachand | 436/169 |
| 5,174,963 | 12/1992 | Fuller et al. | 422/82.05 |
| 5,179,005 | 1/1993 | Phillips | 435/14 |
| 5,200,317 | 4/1993 | Georgevich | 435/7.4 |
| 5,200,321 | 4/1993 | Kidwell | 435/7.9 |
| 5,202,268 | 4/1993 | Kuhn | 436/525 |
| 5,204,063 | 4/1993 | Allen | 422/58 |
| 5,208,147 | 5/1993 | Kagemow et al. | 435/14 |
| 5,212,060 | 5/1993 | Maddox | 435/7.1 |
| 5,213,965 | 5/1993 | Jones | 435/11 |
| 5,215,886 | 6/1993 | Patel et al. | 435/11 |
| 5,218,312 | 6/1993 | Moro | 324/711 |
| 5,223,219 | 6/1993 | Subramanian | 422/55 |
| 5,223,220 | 6/1993 | Fan et al. | 422/58 |
| 5,232,668 | 8/1993 | Grant | 422/82.05 |
| 5,234,813 | 8/1993 | McGeehan | 435/7.9 |
| 5,248,619 | 9/1993 | Skold et al. | 436/514 |
| 5,264,180 | 11/1993 | Allen et al. | 422/56 |
| 5,334,513 | 8/1994 | Skold et al. | 435/7.92 |
| 5,340,539 | 8/1994 | Allen et al. | 422/56 |
| 5,354,692 | 10/1994 | Yang et al. | 436/514 |
| 5,409,664 | 4/1995 | Allen | 422/56 |
| 5,416,000 | 5/1995 | Allen et al. | 435/7.92 |
| 5,451,504 | 9/1995 | Fitzpatrick | 435/7.2 |
| 5,451,507 | 9/1995 | Skold et al. | 435/7.92 |
| 5,468,647 | 11/1995 | Skold et al. | 436/514 |
| 5,580,794 | 12/1996 | Allen | 436/169 |

FOREIGN PATENT DOCUMENTS

| | | |
|---|---|---|
| 0317070 | 5/1989 | European Pat. Off. . |
| 0323605 | 7/1989 | European Pat. Off. . |
| 0330517 | 8/1989 | European Pat. Off. . |
| 0342913 | 11/1989 | European Pat. Off. . |
| 0421294 | 4/1991 | European Pat. Off. . |
| 0430395 | 6/1991 | European Pat. Off. . |
| 8000173 | 1/1980 | Netherlands . |
| 8001515 | 7/1980 | WIPO . |
| 8808534 | 11/1988 | WIPO . |
| 9010869 | 9/1990 | WIPO . |
| 9114942 | 10/1991 | WIPO . |
| 9201226 | 1/1992 | WIPO . |
| 9201498 | 6/1992 | WIPO . |

OTHER PUBLICATIONS

Home Cholesterol Testing, Editorial, The Lancet, vol. 340, Dec. 5, 1992, No. 8832, p. 1386.

Reliability and Feasibility of Pregnancy Home–Use Tests: Laboratory Validation and Diagnostic Evaluation by 638 Volunteers, Joelle Daviaud, Dominique Fournet, Chantal Ballongue, Guy–Pierre Guillem, Alain Leblanc, Claude Casellas, and Bernard Pau, Clin. Chem. 39/1, 53–59 (1993).

A Multilayer Membrane System for Blood Plasma Isolation for use in Primary Health Care, APM Van Oudheusden and HDW Roesink, Ann Clin Biochem 1991; 28:55–59.

Instrument–Free Quantitative Test Systems, Michael P. Allen and Prithipal Singh, Applications of Diagnostics, pp. 147–176 (1990).

ELECTRONIC ASSAY DEVICE AND METHOD

RELATED APPLICATIONS

The present application is a continuation-in-part of prior application Ser. No. 08/455,236, filed May 31, 1995 and now U.S. Pat. No. 5,580,794 issued on Dec. 3, 1996, which is a continuation of application Ser. No. 08/111,347, filed Aug. 24, 1993 and now abandoned. The present application adds and claims additional disclosure not presented in the prior applications.

The subject matter of this application is related to a disposable single-use digital electronic instrument that is entirely self-contained, including all chemistry reagents, as disclosed in U.S. application Ser. No. 08/512,844 entitled "Dry Reagent Particle Assay And Device Having Multiple Test Zones And Method Therefor" filed Aug. 9, 1995 by Joel M. Blatt and Michael P. Allen, U.S. application Ser. No. 08/642,228 entitled "Method And Device For Measuring Reflected Optical Radiation" filed Apr. 30, 1996 by Raymond T. Hebert et al., and U.S. application Ser. No. 08/645,453 entitled "Method And Device Producing A Predetermined Distribution Of Detectable Change In Assays" filed May 11, 1996 by Joel M. Blatt et al. The above applications have the same assignee as the present invention and is incorporated herein by reference in its entirety.

FIELD OF THE INVENTION

This invention relates to a disposable self-contained, electronic assay device for use in determining the amount of one or more analytes in a body fluid such as blood or urine. In particular, this invention relates to a small disposable, electronic credit-card sized device which, upon application of a body fluid to a sample receptor, automatically performs an analysis and presents the concentration of the analyte and/or another message output in readable form.

BACKGROUND OF THE INVENTION

Qualitative and quantitative self-tests have developed gradually over the last half century. An advancement in non-instrumented tests came with the application of immunochemical reagents on a solid support. This led to a number of commercially useful diagnostic tests including those for HCG (pregnancy), LH, FSH, CKMB, Staphylococcus, and Rubella. Measurement of the hormone HCG to detect pregnancy was among the first of these tests to become commercially successful in the home market. The first home pregnancy test, the e.p.t.™ used a solution phase chemical reaction that formed a brown ring on the surface of the urine solution in the presence of HCG. The 2 hour long protocol associated with this test was sensitive to vibration and timing, causing false results.

Two additional test systems that appeared in the late 1980s were the LipoScan™ by Home Diagnostics Inc. and the Chemcard™ by Chematics Inc. Both tests measure cholesterol in whole-blood using visual color comparison. Since visual color matching is subjective, these tests do not achieve the quantitative performance necessary for cholesterol testing (Pradella et al, Clin. Chem. 36:1994–1995 (1990)).

For many analytes such as the markers for pregnancy and ovulation, qualitative or semi-quantitative tests are appropriate. There are, however, a variety of analytes that require accurate quantification. These include glucose, cholesterol, HDL cholesterol, triglyceride, a variety of therapeutic drugs such as theophylline, vitamin levels, and other health indicators. Generally, their quantification has been achieved through the use of an instrument. Although suitable for clinical analysis, these methods are generally desirable for point-of-care testing in physicians offices rather than the home due to the expense of the instrument.

Recently, a number of non-instrumented methods for measurement of analytes have started to emerge. The key to achieving instrument-free quantification is through the use of migration distance, rather than color matching, as the visual signal. In migration distance assays, chemical/biochemical reactions occur as the analyte is wicked through a solid support. During wicking, the analyte reacts with a signal-producing reagent and forms a visible signal along the support. The migration distance or the distance of signal border is related to analyte concentration. The operator reads the height of the color bar, much the same way one reads a thermometer, and finds the concentration from a calibrated scale.

There are a few migration-type assays commercially available. These include Environmental Test Systems' Quantab™, which measures chloride in swimming pools and during the mixing of concrete, Syva's AccuLevel® for the measurement of therapeutic drugs, and ChemTrak's AccuMeter® for measurement of cholesterol in whole blood. Other companies such as Enzymatics and Crystal Diagnostics have more recently announced the introduction of their Q.E.D.™ and Clinimeter™ technologies to measure, respectively, alcohol in saliva and cholesterol in blood. ActiMed™ Laboratories disclose a thermometer-type cholesterol assay device in Ertinghausen, U.S. Pat. No. 5,087,556 (1992).

Although these single use, thermometer-type, non-instrumented quantitative devices and non-instrumented color comparison devices for qualitative measurement have shown adequate performance, they have several problems associated with reliability and convenience. First, the colors generated on these devices are not always uniform and sharp. In the case of migration type assays the border is often light in color, unclear and difficult to read. This translates directly into user errors since the user must make a judgment related to the position of the color band border. In the case of non-instrumented pregnancy tests it is sometimes difficult to visually interpret the intensity of the colored spot (especially at HCG concentrations close to the cut-off sensitivity), and interpretation of the result is sometimes a problem. Anytime a non-technical operator is required to make a visual judgment or interpretation, an error is possible and, sometimes, unavoidable.

Second, the assay protocol for these tests is sometimes difficult and lengthy, taking 15 minutes to 1 hour to obtain a result. Third, these tests often do not have sufficient procedural and reagent references to assure adequate test performance. Fourth, non-instrumented devices can only measure single endpoint type tests since enzyme rates or ratiometric analysis of two analytes cannot be measured. Therefore, the test menu of potential analytes is limited.

As an example of the significance of the problems, a recent article in Clinical Chemistry (Daviaud et al, Clin. Chem. 39:53–59 (1993)) evaluated all 27 home use pregnancy tests sold in France. The authors state, "among the 478 positive urine samples distributed, 230 were falsely interpreted as negative".

Thus, a need exists in the field of diagnostics for a single-use assay which is sufficiently accurate and reliable to permit point-of-care use by untrained individuals in locations such as the home, sites of medical emergencies, or locations other than a clinic.

SUMMARY OF THE INVENTION

The present invention provides an assay device for determining the presence of one or more selected analytes in a sample. The device includes a housing having an exterior surface and defining an interior area. A sample receptor means receives the sample and is located on the exterior surface of the housing. The sample treatment means reacts the sample with a reagent to yield a physically detectable change which correlates with the amount of selected analyte in the sample. The sample treatment means is located within the housing and is in fluid communication with the sample receptor means. The device also includes a detector means which responds to the physically detectable change and produces an electrical signal which correlates to the amount of the selected analyte in the sample. The detector means is located within the housing and is in electrical or optical communication with the sample treatment means. A processing means converts the electrical signal to a digital output and is located within the housing and connected to the detector means. A starting means automatically activates the processing means and detector means upon the application of the sample to the device. The starting means is located within the housing and connected to the processing means. A display means visually displays the digital output external to the housing and is connected to the processing means.

One preferred embodiment of the present invention provides a multi-assay device for determining the presence of a plurality of selected analytes in a sample. The multi-assay device includes a housing having an exterior surface and defining an interior area. A sample receptor means receives the sample and is located on the exterior surface of the housing. A sample treatment means reacts the sample with a plurality of reagents corresponding to the plurality of selected analytes to yield physically detectable changes which each correlate with the amount of one of the selected analytes in the sample. The sample treatment means is located within the housing and is in fluid communication with the sample receptor means. A detector means responds to the physically detectable change and produces electrical signals which each correlate to the amount of one of the selected analytes in the sample. The detector means is located within the housing and is in electrical or optical communication with the sample treatment means. A processing means converts each electrical signal to a digital output corresponding to one of the selected analytes and is located within the housing and connected to the detector means. The device includes a display means which externally displays the digital output corresponding to one of the selected analytes. Each digital output corresponding to one of the selected analytes includes at least a first component providing the assay results such as the identity of the selected analyte and a second component providing the amount of the selected analyte. The display means is connected to the processing means.

Another preferred embodiment of the present invention provides an assay device which provides quantitative measurement of one or more selected analytes in a sample using reflected optical radiation. The device includes a housing having an exterior surface and sealing an interior area. A receptor is configured to receive the sample containing the analyte selected for determining its presence and is located on the exterior surface of the housing. At least one assay strip reacts the sample with a self-contained reagent to yield a physically detectable change in at least one sampling area on each assay strip which correlates with the amount of selected analyte in the sample. Each assay strip is in fluid communication with the receptor. A reflectometer is included in the device which has an optical radiation source, a detector configured to quantitatively detect optical radiation, and an optics assembly configured to direct the illumination from the optical radiation source to each sampling area and to direct the radiation diffusely reflected from each sampling area to the detector. The detector produces electrical signals which correlates to the amount of one of the selected analytes in the sample. A processor is configured to store assay calibration information which is uniquely characteristic to each specific self-contained reagent and physically detectable change within each sampling area and to the specific reflectometer of the individual assay device. The processor is further configured to calibrate each sampling area and the reflectometer using the stored assay calibration information. The processor is further configured to convert the electrical signal to a digital output. The processor is sealed within the housing and connected to the reflectometer. A starter is configured to automatically activate the processor and reflectometer upon the application of the sample to the device. The starter is located within the housing and connected to the processor. A display is configured to visually display the digital output external to the housing and is connected to the processor.

The present invention also provides a method for determining the presence of one or more selected analytes in a sample within a disposable housing. The method includes the steps of: reacting the sample within the housing with a reagent corresponding to the selected analyte to yield a physically detectable change which correlates with the amount of the selected analyte in the sample; calibrating the physically detectable change using assay calibration information uniquely characteristic to each specific reagent in the housing and to the physically detectable change for each selected analyte to determine the amount of the selected analyte; and, displaying the amount of each selected analyte.

Another method provided by the present invention automatically starts a diagnostic device to analyze a sample. The method includes the steps of: sensing the introduction of a sample to the device and generating a signal to activate the device. Preferably, the sensing step includes creating a potential between a plurality of electrodes and changing the electrical potential between the electrodes upon contacting the electrodes with the sample.

The present invention also provides a method of displaying quantitative assay results for a plurality of selected analytes in a sample on a diagnostic device. The method includes the steps of: simultaneously displaying the identity and amount of one of the selected analytes for a predetermined period of time; and, repeating the prior step for another one of the plurality of selected analytes.

The advantages, embodiments, variations and the like of the present invention will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
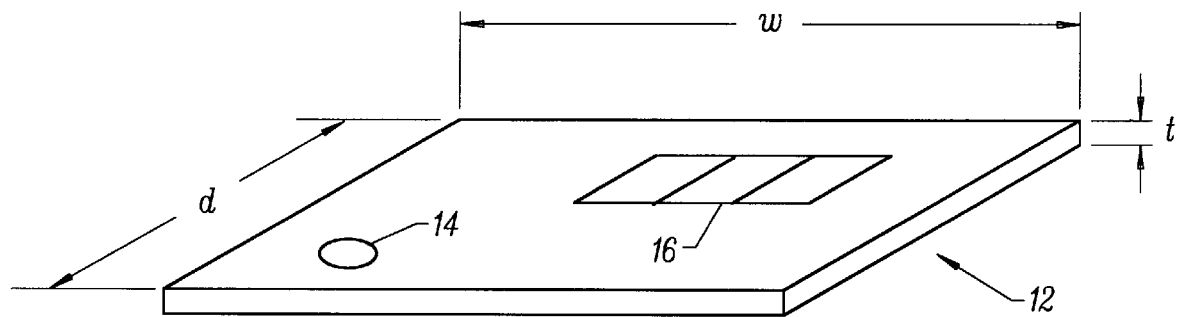
FIG. 1 is an isometric view of an embodiment of the disposable device of this invention.

The present invention represents a substantial improvement in the art by providing assay methods and devices that can produce qualitative or quantitative results. The assay chemistry is self-contained within the instrument and dry formulated on a solid matrix (i.e. membrane) where reflectance is used, or lyophilized and deposited or spotted and dried in a reaction compartment where transmission is used, or present on an electrode where the chemistry produces a change in electrical current or pH. The chemistry operates in response to the analyte to produce a color change within the chemistry matrix or in a fluid defined by the sample (i.e. plasma) and reconstituted reagents. Alternately, the chemistry will produce a change in electric current (i.e. produce or consume electrons, or cause changes in electrical conductivity) or cause a pH change that can easily be detected. This type of chemistry is common in home glucose instruments that contain chemistry reagents impregnated in a reagent strip.

Substantially all types of assays can be carried out with the present invention for a wide variety of analytes. Assays that can be performed include, but are not limited to, general chemistry assays and immunoassays. Both endpoint and reaction rate type assays can be accomplished with the present invention.

Analyte, as used herein, is the substance to be detected which may be present in the test sample. For example, general chemistry assays can be performed for analytes such as, but not limited to, glucose, cholesterol, HDL cholesterol, LDL cholesterol, triglycerides, and BUN. For immunoassays, the analyte can be any substance for which there exists a naturally occurring specific binding member (such as, an antibody), or for which a specific binding member can be prepared. Thus, an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. In particular, such analytes include, but are not intended to be limited to, ferritin; creatinine kinase MB (CK-MB); digoxin; phenytoin; phenobarbital; carbamazepine; vancomycin; gentamicin, theophylline; valproic acid; quinidine; luteinizing hormone (LH); follicle stimulating hormone (FSH); estradiol, progesterone; IgE antibodies; vitamin B2 micro-globulin; glycated hemoglobin (Gly Hb); cortisol; digitoxin; N-acetylprocainamide (NAPA); procainamide; antibodies to rubella, such as rubella-IgG and rubella-IgM; antibodies to toxoplasma, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B antigen (HBAg); antibodies to hepatitis B antigen (Anti-HB); thyroid stimulating hormone (TSH); thyroxine (T4); total triiodothyronine (Total T3); free triiodothyronine (Free T3); carcinoembryonic antigen (CEA); and alpha fetal protein (AFP). Drugs of abuse and controlled substances include, but are not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone, and opium; phencyclidine; and propoxyphene. The details for the preparation of such antibodies and their suitability for use as specific binding members are well known to those skilled in the art.

The present invention provides assays which preferably use specific binding members. A specific binding partner or member, as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies, and antibody fragments, both monoclonal and polyclonal, and complexes thereof, including those formed by recombinant DNA molecules. The term hapten, as used herein, refers to a partial antigen or non-protein binding member which is capable of binding to an antibody, but which is not capable of eliciting antibody formation unless coupled to a carrier protein.

The analyte-analog can be any substance which cross-reacts with the analyte-specific binding member, although it may do so to a greater or lesser extent than does the analyte itself. The analyte-analog can include a modified analyte as well as a fragmented or synthetic portion of the analyte molecule, so long as the analyte-analog has at least one epitope site in common with the analyte of interest. An example of an analyte-analog is a synthetic peptide sequence which duplicates at least one epitope of the whole-molecule analyte so that the analyte-analog can bind to an analyte-specific binding member.

The sample to be tested by the present invention for the presence of an analyte can be derived from any biological source, such as a physiological fluid, including whole blood or whole blood components including red blood cells, white blood cells, platelets, serum and plasma; ascites; urine; sweat; milk; synovial fluid; peritoneal fluid; amniotic fluid; cerebrospinal fluid; and other constituents of the body which may contain the analyte of interest. The test sample can be pre-treated prior to use, such as preparing plasma from blood, diluting viscous fluids, or the like; methods of treatment can involve filtration, distillation, concentration, inactivation of interfering compounds, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte. The analyte can be any compound or composition to be detected or measured and which has at least one epitope or binding site.

Single or multiple assays can be done at one time. For example, a single assay can be performed measuring cholesterol or one device can be set up to measure both total and HDL cholesterol from a single sample. One test device can be set up to measure one, two, three, or more analytes at one time.

The device of this invention is ideal for on-site testing in remote locations throughout the world in health fairs, occupational health settings, physician offices, and in the home. The device can include automatic reagent handling (sample filtration, component separation, blood separation or the like), automatic sample measurement, automatic reagent delivery, and on-board controls such that non-technical users can operate the test easily without prior training. Also since the device uses a digital display (like a calculator) there is no need for visual interpretation of color quality or intensity, or visual reading of a signal migration distance. Thus, user errors will be significantly reduced using this disposable electronic device.

One of the key features of this invention is the inexpensive cost of the device such that it becomes economically practical for the device to be used as a single, disposable unit. The device includes an electronic component, a chemistry reagent component, and a housing which contains the electronics and chemistry. It is desirable that the electronics and housing are integrated into a single piece. However, the reagent strip can be replaced once or several times such that the electronics component is re-used.

Referring to the drawings, FIG. 1 is an isometric view of one embodiment of the disposable device of this invention. The device 12 has a sample receptor 14 and a visual readout display 16 such as a liquid crystal display. The thickness "t", width "w" and depth "d" can be varied to provide the desired overall dimensions. The device 12 can be of any convenient size with the optimal dimensions determined by several factors including, but not limited to: 1) the size of the electronic components, 2) the size of the chemistry components, and 3) marketing consumer studies. The device 12 may assume any convenient shape including square, rectangle, triangle, oval, round, or any other desired shape as long as the electronics and chemistry can be cost effectively contained with acceptable performance.

The instrument is designed for a single use and can measure, for example, transmission, reflectance, electrical conductivity, electrical current or pH change. The instrument is fabricated in a unitized integrated format to reduce the cost of manufacture. The instrument may have the following generally described components: light source such as a light emitting diode (LED); optics; a detector which senses reflected or transmitted light; a processor with memory which controls the assay start and stop, receives and processes input from the detector, stores assay calibration information and the like; an analog to digital converter or the like (a current integrating comparator can be used); a power source which can be a battery or solar cell or any convenient power source; a temperature compensation mechanism (optional); and a liquid crystal display (LCD) with 1 to 6 digits (preferably 3½ digits). The instrument described may contain one, all, or none of the above-mentioned components or may contain other components that are necessary for the diagnostic reflectance or transmission instrument to operate.

Figure 2:
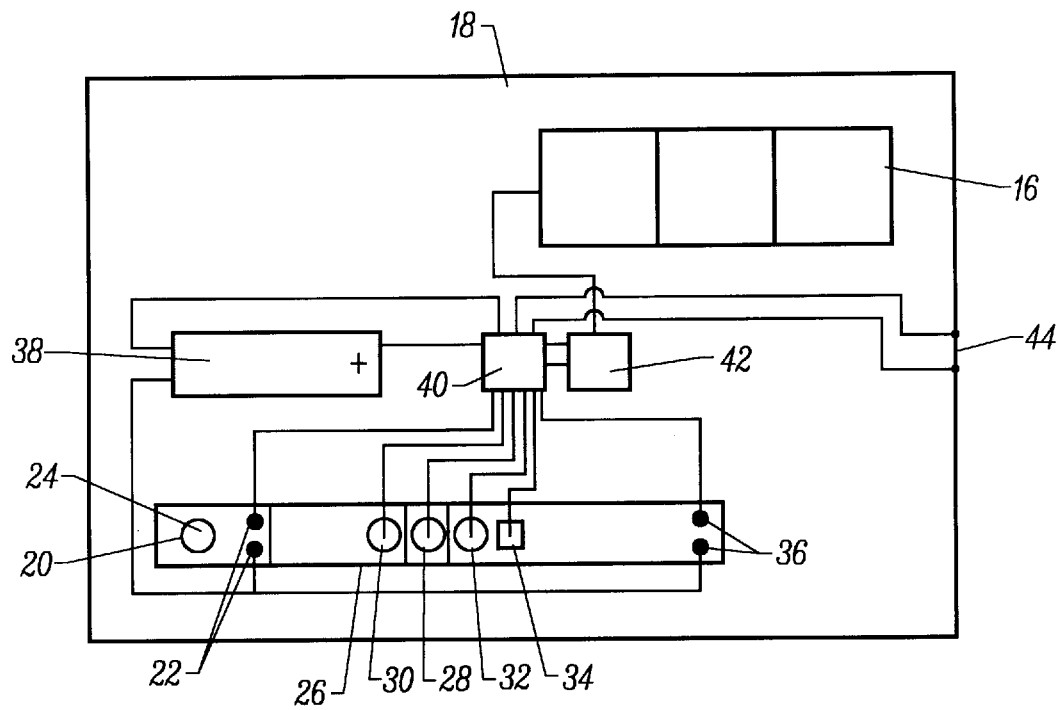
FIG. 2 is a schematic view of the device of this invention, showing one configuration of the electronic and sample processing components for single analyte testing.

FIG. 2 is a schematic view of the device 12 of this invention designed for reflectance measurement of a detectable signal, showing one configuration of the electronic and sample processing components for single analyte testing. Mounted in a housing 18 are all of the components, including a power supply 38 required to conduct the assay. A reagent strip 20 has an electrode pair 22 mounted thereon between a sample application zone 24 and a reagent zone 26, or at the site of the sample application, to detect the presence and movement of sample liquid on the reagent strip 20. Presence of sample liquid bridging the electrode pair 22 reduces the resistance across the electrodes, signaling the presence of a conductor (sample liquid) therebetween. An LED 28 is positioned between the detectors 30 and 32. The detectors 30 and 32 are conventional light detectors which detect light reflected at a preselected wavelength corresponding to a property of the physically detectable label. Temperature sensor 34 is mounted on the reagent strip to detect the temperature of the system and provide ambient temperature information for calibration adjustment at temperature extremes. It is suitable to locate the temperature sensor anywhere in or on the device. For example, the temperature sensor may be located on the microprocessor. The electrode pair 36 is positioned to detect movement of sample liquid beyond the detection zone occupied by the light sensors.

The power supply 38 has a lead from its negative pole connected to one side of the electrode pairs 22 and 36, and a lead from its positive pole being connected to an analog to digital converter 40 and display 16. A processor and memory component 42 is connected to the analog to digital converter 40 and the display 16. External calibration ports 44 are connected to the analog to digital converter 40.

This embodiment of FIG. 2 includes two sets of electrodes (22 and 36) which function to turn the instrument on in one of two modes when the sample is present by using the conducting properties of the sample to complete the circuit between the electrodes. Electrode set 22 is the "reference-on" electrode which is positioned immediately downstream from the sample application port. The sample comes into contact with this electrode set almost immediately after application onto the device. The instrument calibrating-to-self-zero feature is energized allowing the light source to warm up and the optical system (LED, detector, and optics) to zero by taking readings on the unreacted reagent area. Electrode set 36 is called the "read-on" electrode which is positioned at the end of the chemistry reagent, and is downstream from the electrode set 22 and downstream from the optical system. When the sample reaches this electrode set the chemical reactions are well underway and the instrument begins to read the reagent system. The reading may begin immediately when the sample reaches electrode set 36 or there may be some time delay of about less than 1 second to 10 minutes (preferably from about 30 seconds to 2 minutes). There may be single or multiple readings or the readings may continue until the reagent system response has stabilized either to an endpoint, maximum or minimum, or to a constant reaction rate. These readings may be initiated by either electrode set 22 or 36.

As described above, the electrode set 35 indicates that sufficient sample was introduced to the device and has been transported across the reagent strip. Use of the electrode set 35 is optional.

The instrument functions of "automatic zero" and "read" are initiated in response to the presence of a sample. The electrode method is described above; however, any convenient and inexpensive method can be used. Another method uses a solar cell which activates when the device is removed from the light-impermeable foil storage pouch. When the user removes the device from the pouch the ambient light turns the instrument on, activates the self-reference and allows the LED and optics to warm up. This also initiates a timer on the processor which automatically activates the "read on" function after a specified time. This system eliminates the need for the "reference on" and "read on" electrode pairs.

Although the auto start configuration of the present invention may be used in an integrated assay device, the present invention can be used in any other instrumented reflectance or transmission meter, potentiometric, amperometric, conductimetric or pH meter or the like, as part of a replaceable reagent. Thus, the auto start embodiment of the present invention also encompasses non-integrated assay instruments and analytical assay instruments comprising the present assay device.

The optics are optional for some embodiments of the present invention. The optical system may include a light source such as an LED, a detector and an optical surface. The optical surface may be as simple as a clear or transparent coating over the light source and detector. A simple aperture can be used in lieu of a lens to focus and meter the light. The coating can be any plastic, silicone, glass, or the like. The optical system of the device may be set up to measure single or multiple analytes. For single analytes only one light source and detector are necessary; for two analytes, two sets of light source and detector may be used and so on.

The processor 42 can be any common or custom integrated circuit with memory. The processor 42 must have the capacity to either store a set of pre-programmed calibration curves or have the capability to be programmed during device manufacturing. In the case of preprogrammed calibration, a method of curve selection during manufacture is necessary. This can be done by laser burning of a selection of circuit pathways or any convenient means. In the case of post-manufacture calibration, a method to load calibration data onto the chip is necessary, for example external calibration contacts 44. External calibration can be accomplished with external electrical contacts or may be done with a non-contact method using radio waves, magnetic fields, pulse light, laser or the like. The non-contact method of calibration may be more practical and efficient from a manufacturing viewpoint.

The processor 42 will also control the entire operation of the instrument including, but not limited to, turning the instrument "reference-on" and "read-on" in response to electrode power or time signals; timing, recording, and processing the instrument zero function; controlling any time delays or timed steps during reading; determining when the reaction has stabilized; receiving and processing information from the temperature sensor; and receiving input from the optical system and converting it to output, based on calibration information, to the display. The processor can also calculate the time taken for the sample to travel from electrode set 22 to electrode set 36 and if too much time is taken an error code will show on the display. The processor will also determine if the chemistry reaction has occurred within the specified time, to a specified endpoint range or within a specified reaction rate range to control for inactive reagents. Any other electronic control checks can also be included.

The power supply 38 can be any convenient device including, but not limited to, a battery or a solar cell. The shelf life of the final product will be about 6 months to about 24 months at room temperature. The power supply must have stability consistent with this shelf life. Use of a solar cell would have the advantage of allowing the instrument to initiate and automatically zero itself immediately after the assay device is taken out of the storage foil pouch. This would eliminate the need for electrode set 22 ("reference-on" electrodes).

The display 16 preferably is a liquid crystal device LCD or any conventional, inexpensive display device. The number size in the display should be sufficiently large to allow most people to read the assay value, even if they have poor vision. The display height may be from about 0.5 to about 2.0 cm and most likely from about 0.75 cm to about 1.5 cm. The number of digits in the display can be anywhere from 1 to about 10 digits, however, most assays require only 3½ digits and therefore the display in this device will likely have a 3 to 5 digit display. In addition to showing the assay result, the display may show messages such as "SAMPLE VOLUME OK" and "RESULT OK".

In the case of measuring one analyte, only one display is usually necessary. In the case where two or more analytes are measured simultaneously, then at least two display configuration options exist which include a single display which alternates between results with only one result on the display at one time, or two or more results being shown on the display at one time. For example, if both total cholesterol and HDL cholesterol are measured then the display can alternate between the total and HDL values or show both values at one time. The ideal situation would be having all values displayed simultaneously. However, manufacturing cost is a consideration.

Figure 3:
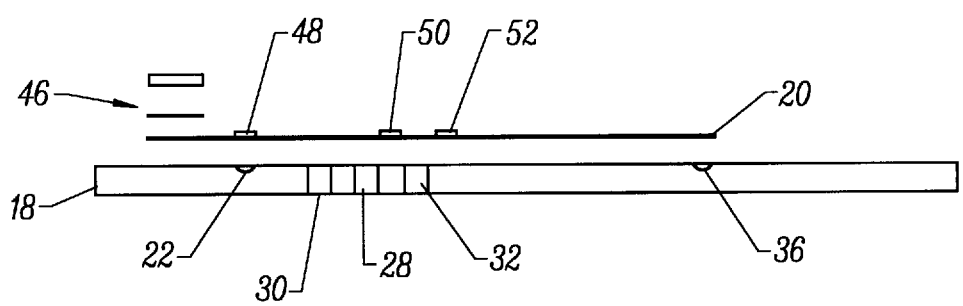
FIG. 3 is an exploded cross-sectional side view of one configuration of the sample processing components for single analyte testing.

FIG. 3 is an exploded cross-sectional side view of one configuration of the sample processing components for single analyte testing. The reagent strip 20 rests on a lower plate of housing 18 supporting the electrodes 22 and 36, LED 28 and detectors 30 and 32. A separation device 46 rests on the input end of strip 20. The strip 20 includes a plurality of zones 48, 50 and 52, the functions of which will be described in detail hereinafter.

The chemical reagents are dry formulated on the reagent strip 20 which can be any convenient bibulous material including, but not limited to, fabric or mesh made of cotton, nylon, polyester, polypropylene, polyethylene or the like; paper such as Whatman 1C, 2C, 31ET or 3MM, or S&S 903C, 470, 604 or the like; glass fiber such as Whatman GFA or GFD, or S&S 3362 or 32; plastic fiber, metal fiber, or any hydrophilic synthetic membrane; synthetic membranes such as Millipore IMMOBILON, Pall nylon, S&S nitrocellulose, cellulose acetate, regenerated cellulose, Gelman VERSAPORE or the like. The reagent strip 20 can also be made of any convenient bibulous material including porous plastics such as polyethylene and polypropylene, examples of which are made by Porex Technologies Corp., or synthetic or natural mesh screens, examples of which are made by Tetko. By "porous" is meant that the material is one through which the test sample can easily pass and includes both bibulous and non-bibulous solid phase materials.

An assay device for the present invention can have many configurations, several of which are dependent upon the material chosen as the reagent strip 20. Other configurations of the reagent strip include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., polyethylene sheet material).

In a preferred embodiment, the present dry reagent assay device uses a lateral flow bibulous material with proximal and distal ends, containing at least one central zone along its length. The strip configuration may be of any dimensions which provide the desired number of zones and which permit (a) the desired binding or chemical reactions to be completed in a reproducible manner and (b) detection of the reaction indicator to occur. Preferably, the present strip is a total of no more than about 100 mm in length and about 6 mm wide, and more preferably, from about 10 mm to about 40 mm in length and about 1 mm to about 5 mm wide.

The bibulous strip can comprise a plurality of zones along its length. Each zone can be from about 0.1 mm to about 10 mm wide, more preferably from about 1 mm to about 5 mm wide. There will be a minimum of two zones and a maximum of about 10 or more zones, depending on the number of assays to be conducted on one bibulous strip. The strip can be one continuous section or composed of one, two, three or more sections. Each zone may be a separate bibulous material, all in fluid communication, or one or more zones can be a common material with the other zones being made of separate materials.

The assay devices include a bibulous substrate to which members of specific binding pairs, which may be labeled, are diffusively or non-diffusively immobilized. Non-diffusive immobilization can be conducted by adsorbing, absorbing, crosslinking or covalently attaching a reagent such as an unlabeled member of a binding pair to the bibulous substrate.

Diffusive immobilization can be conducted by formulating the assay reagent(s) to be immobilized (e.g., by dissolving in a suitable solvent such as water, a $C_1$–$C_4$ alcohol or mixture thereof, along with any desired additives), applying the resulting formulation to the bibulous material of the membrane, filter or transport layer in the desired location(s), and drying the material. Diffusive immobilization allows rapid reconstitution and movement of reagents, whether reacted or unreacted, through the bibulous substrate. Suitable additives may include detergents, proteins, blocking agents, polymers, sugars or the like. Alternatively, the additive(s) and assay reagent(s) may be applied to the membrane, filter or transport layer by precoating with a "blocking agent", water soluble polymer, sugar or detergent, followed by depositing the conjugate or conjugate formulation and drying the material.

The separation device 46 for filtering the sample from unwanted contaminants such as red cells in blood can be constructed using synthetic membranes, fibrous depth filters such as glass fiber, plastic fiber, metal fiber, cellulose fiber or the like or any combination of filters and membranes. For example, the separation device 46 can include micro-porous synthetic membranes of pore size from about 0.2 $\mu$m to about 12 $\mu$m (preferably about 0.4 $\mu$m to about 7 $\mu$m). Examples include: Pall nylon, S&S nitrocellulose, cellulose acetate, regenerated cellulose, nucleopore Poretics or the like. The separation materials may be untreated or can be coated with proteins, dextrans, sugars, or carbohydrates for red cell stabilization, LDL precipitating reagents such as magnesium chloride and dextran sulfate, antibodies, or red cell agglutinating agents to facilitate red cell removal. The sample transport area can be untreated or have various reagents diffusively or non-diffusively immobilized, such as stabilizing proteins, detergents, anticoagulants like heparin or EDTA, LDL precipitating reagents, antibodies, or red cell agglutinating agents like wheat germ lectin or anti-human RBC.

The housing 18 of the device can be made of any conventional material including, but not limited to, thermoplastics such as polyethylene, Delrin, ABS and polystyrene.

For immunoassays, the present invention preferably uses particle detection for a detectable response or signal in each test zone related to the level of analyte in the sample. Other means for providing a detectable response in the test zones are suitable for use in the present invention. For example, and not for limitation, the analyte may be labeled with an indicator to measure electrical conductance or the reflectance or absorption of a characteristic light wavelength. The analyte may also be reacted with other chemicals to convert a dye, chromogenic compound or the like into a colored form detectable by means of transmission or reflectance photometry. As used herein, "indicator" is meant to include all compounds capable of labeling the analyte or conjugate thereof and generating a detectable response or signal indicative of the level of analyte in the sample.

The present device may be used on-site in the home and in the physician's office, or in remote locations in emergency medicine. Therefore, the device may advantageously include sample pre-treatment as previously defined, as well as a sample withdrawal device (e.g., a fingerstick) or any combination thereof. Sample pretreatment can also adjust the pH to within a specified range, reference salt concentration, turbidity and/or viscosity, and/or reduce or remove interfering substances such as immunochemical cross-reactants, redox substances and the like.

Figure 4:
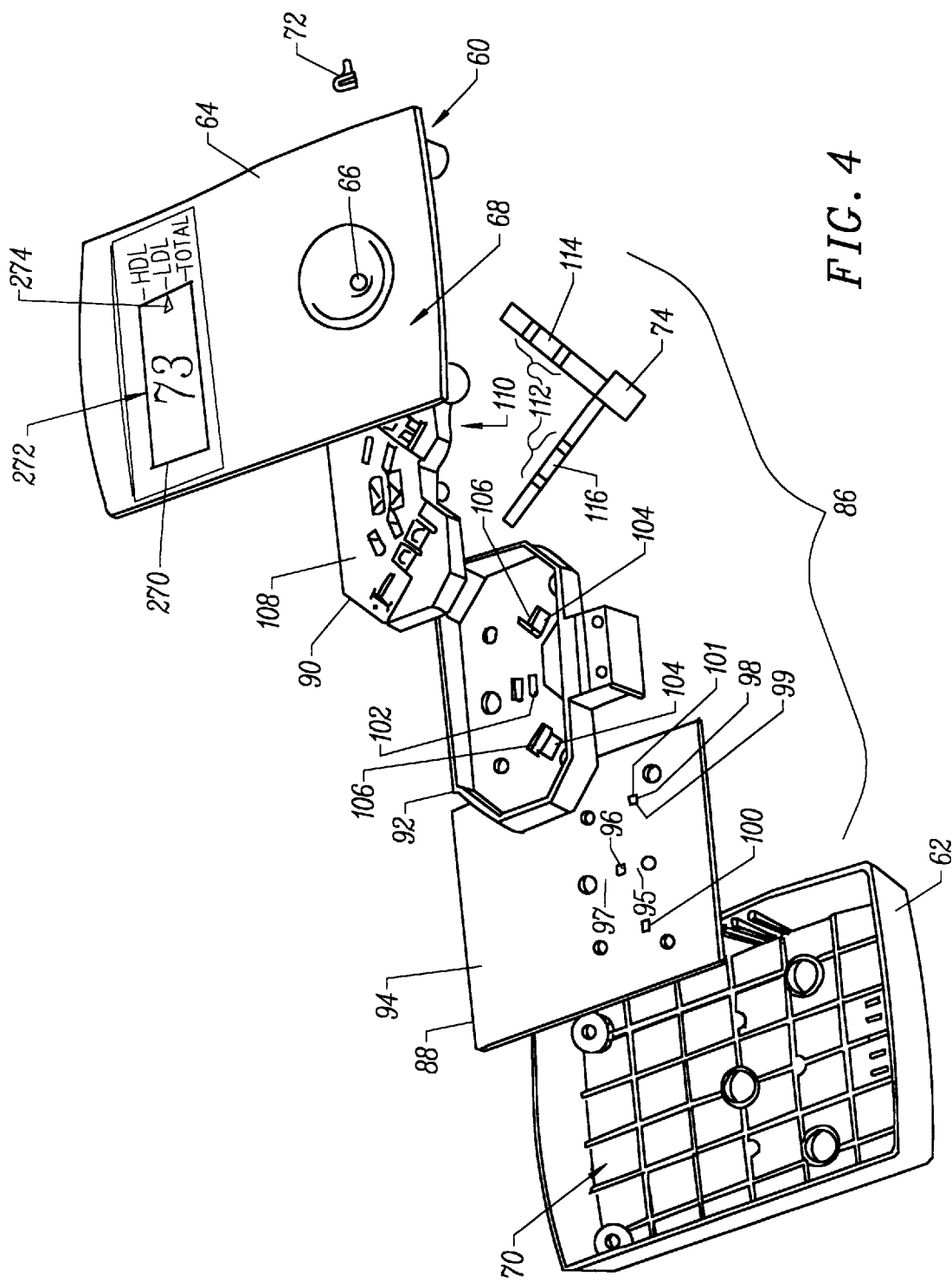
FIG. 4 is an exploded perspective view of a preferred embodiment of a diagnostic device of the present invention.

A preferred embodiment of a single-use diagnostic device 60 is illustrated in FIG. 4. The device 60 includes a housing 62 and cover 64 having a receptor such as inlet port 66 which extends from the exterior surface 68 of the cover to the interior 70 of the housing for receiving a sample 72 containing the one or more selected analytes to be determined.

Figure 5:
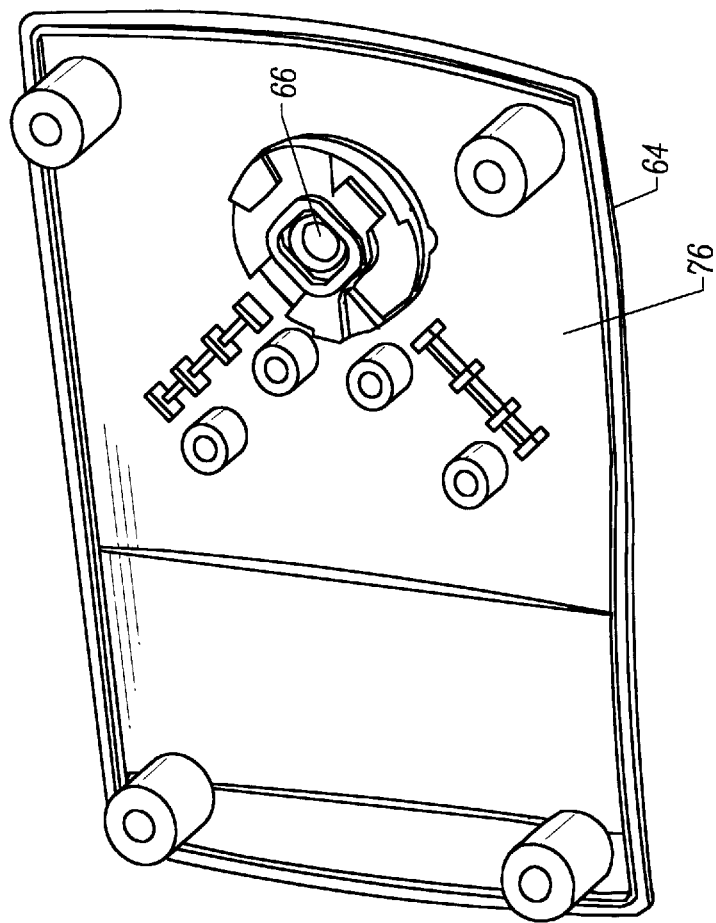
FIG. 5 is an isolated perspective view of the underside of the cover of the device in FIG. 4.

The inlet port 66 allows the sample 72 to be introduced to a sample receiving device 74 which is attached to the interior surface 76 of the cover 64 as seen in FIG. 5. The sample receiving device 74 includes a pad which is in fluid communication with two assay strips and serves to distribute the sample between the two strips. Optionally, the sample receiving device 74 can also include a sample filter pad which removes undesired contaminants from the sample. The sample filter pad can be the same as the receiving pad with one pad performing bother functions. The device 60 can include more than one sample filter pad along the pathway of the sample flow which remove different types of contaminants. The two assay strips contain chemical reagents for determining the presence of one or more selected analytes.

Referring to FIG. 4, the interior 70 of the housing encloses a reflectometer 86 which includes a printed wiring assembly having a printed circuit board (PCB) 88. The reflectometer 86 also includes an optics assembly 90 and a shield 92. The PCB 88 has one face 94 with a reference detector 96 and zone detectors 98, 100 mounted directly thereto. The face 94 of the PCB also has two LEDs 95, 97, one for each pair of illumination channels, mounted directly to the PCB. The LEDs 95, 97 are preferably in bare die form without an integral lens, enclosure, or housing. As a result, the LEDs 95, 97 provide illumination in all directions above the face 94 and are directed only by the optics assembly 90. Similarly, the zone detectors 98, 100 and reference detector 96 are bare die mounted directly to the face 94 of the PCB. The LEDs 95, 97 and the detectors 96, 98, 100 are all positioned in the same plane.

FIG. 4 also illustrates the position of the shield 92 relative to the PCB 88. Aperture 102 is provided through the shield 92 to prevent obstructing the LEDs 95, 97 and the reference detector 96. Openings 104 are provided to prevent obstructing zone detectors 98, 100. The shield 92 includes upstanding walls 106 which prevent stray radiation from entering the zone detectors 98, 100. The upstanding walls 106 are positioned adjacent the reflecting and refracting elements of the optics assembly 90 when the reflectometer 86 is fully assembled.

The optics assembly 90 is a generally planar support having at least a top face 108 and a bottom face 110. The bottom face 110 is configured to receive illumination from the LEDs 95, 97 and the optics assembly 90 directs the illumination to one or more sampling areas 112 on a first 114 and second 116 assay strip. The top face 108 of the optics assembly is also configured to transmit the diffusely reflected optical radiation returning from the sampling areas 112 to one or more of the zone detectors 98, 100.

Figure 6:
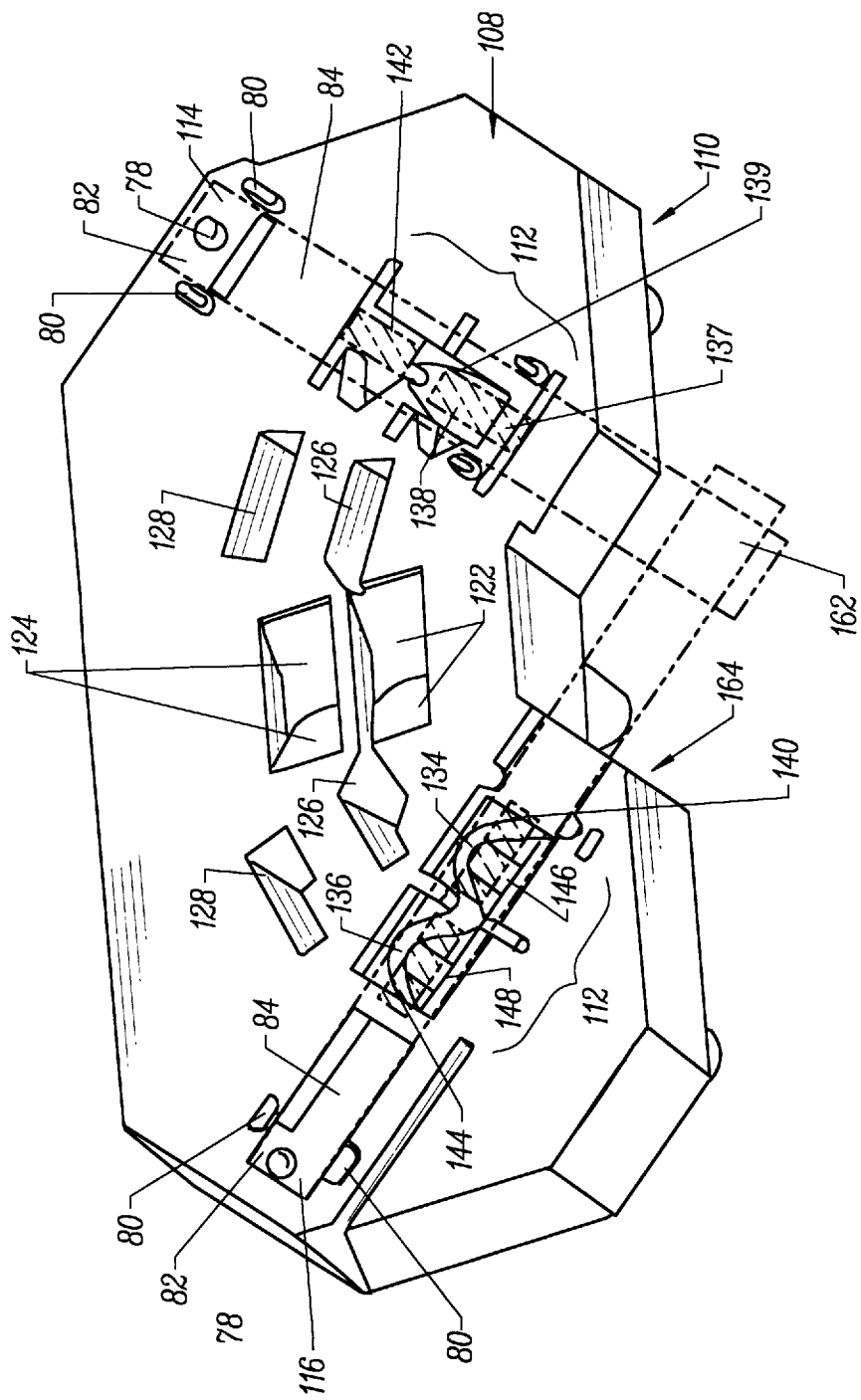
FIG. 6 is an isolated perspective view of the top face of the optics assembly of the device in FIG. 4.

The top face 108 of the optics assembly is shown isolated in FIG. 6 and is configured to transmit illumination directed toward the sampling areas 112 on the first 114 and second 116 assay strips shown in phantom. The top face 108 also transmits the optical radiation diffusely reflected from the sampling areas 112 to one or more of the zone detectors 98, 100. The top face 108 also supports the underside of the first 114 and second 116 assay strips and positions the assay strips over the detectors 98, 100 between the upstanding prongs 80 and by having pins 78 press-fit into corresponding holes located at the distal ends 82 of the assay strips 114, 116.

Figure 7:
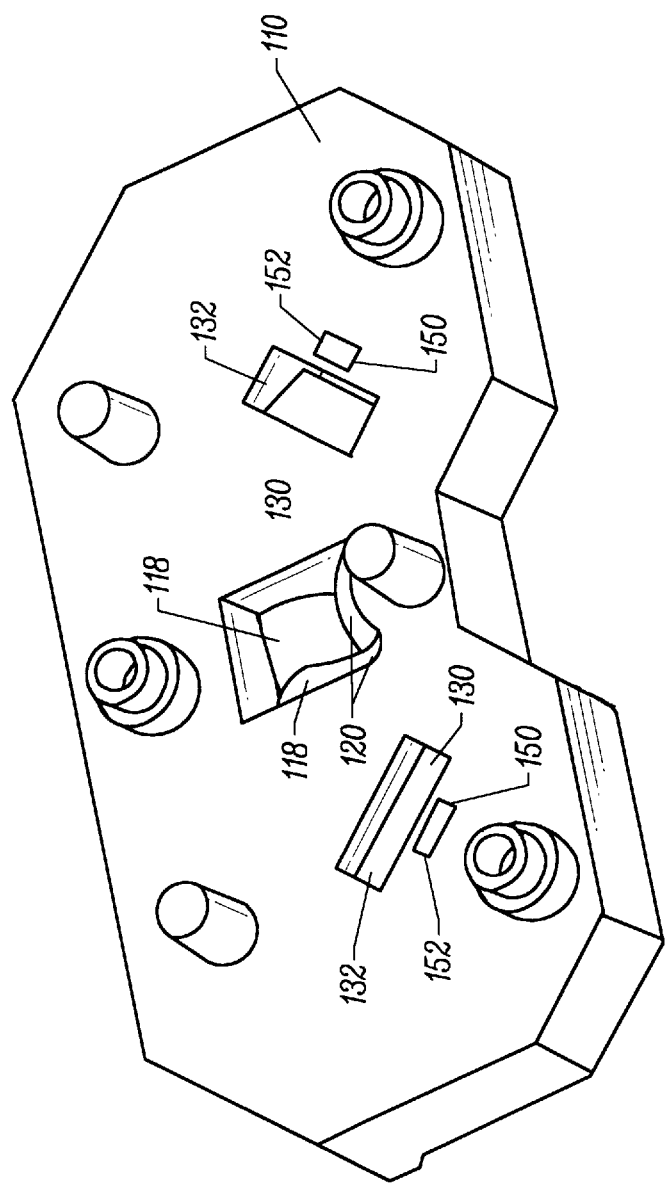
FIG. 7 is an isolated perspective view of the bottom face of the optics assembly of the device in FIG. 4.

The discrete light paths or channels are illustrated with more clarity by referring to the detectors and the LEDs in FIG. 4, and more specifically to FIGS. 6 and 7 isolating the optics assembly. The illumination from each LED 95, 97 located underneath the optics assembly 90 is partially collimated by respective pairs of refracting elements 118, 120. Stray illumination off of the surface of reflecting elements from each LED 95, 97 is directed to reference detector 96. The partially collimated illumination is split into two channels for each pair of refracting elements 118, 120 for a total of two pairs of channels or four individual channels of illumination. Illumination in each pair of channels is then deflected off a series of reflecting element pairs in the following sequence: pairs of reflecting elements 122 and 124, pairs of reflecting elements 126 and 128, and pairs of reflecting elements 130 and 132.

The illumination of each channel is then passed through pairs of refracting elements 134 and 136 which spread the illumination for each channel in a predetermined shape across the sampling areas 112. More specifically, the pair of refracting elements 134 spreads the illumination across first detection zones 138 and 140 on assay strips 114 and 116 respectively. The pair of refracting elements 136 spreads the illumination across second detection zones 142 and 144 on assay strips 114 and 116 respectively.

The diffused optical radiation reflected downward by the first detection zones 138 and 140 is partially collimated by a pair of refracting elements 146. Similarly, the diffused optical radiation reflected downward by the second detection zones 142 and 144 is partially collimated by a pair of refracting elements 148. Pairs of refracting elements 150 and 152 further direct the partially collimated diffuse optical radiation from the refracting elements 146 and 148 to detectors 98 and 100. More specifically, detector 98 receives the diffused optical radiation from the first and second detection zones 138, 142 on the first assay strip 114. Detector 100 receives the diffused optical radiation from the first and second detection zones 140, 144 on the second assay strip 116.

Each pair of refracting elements such as 146 and 150 used for detection zone 138 constitutes an anamorphic lens system which can differentially image the detection zone 138 onto the detector 98 so that the boundaries of detector 98 clearly define boundaries of detection zone 138 in each axis independently. The leading edge 99 and the trailing edge 101 of the detector 98 define the leading edge 137 and the trailing edge 139 of the detection zone 138 with regard to the placement of the chemical reagents on the assay strip 114. The anamorphic lens system is designed to accommodate placement tolerance of the detector die 98 and the LED dies 95 and 97 by differentially magnifying the detection zone 138 onto the detector 98 through anamorphic refractive elements 146 and 150 such that the illumination zone overfills the detection zone 138 in the direction of sample flow and underfills perpendicularly to the direction of sample flow. Furthermore, the present invention intends to provide uniformity of sensitivity throughout the detection zone 138.

Figure 8:
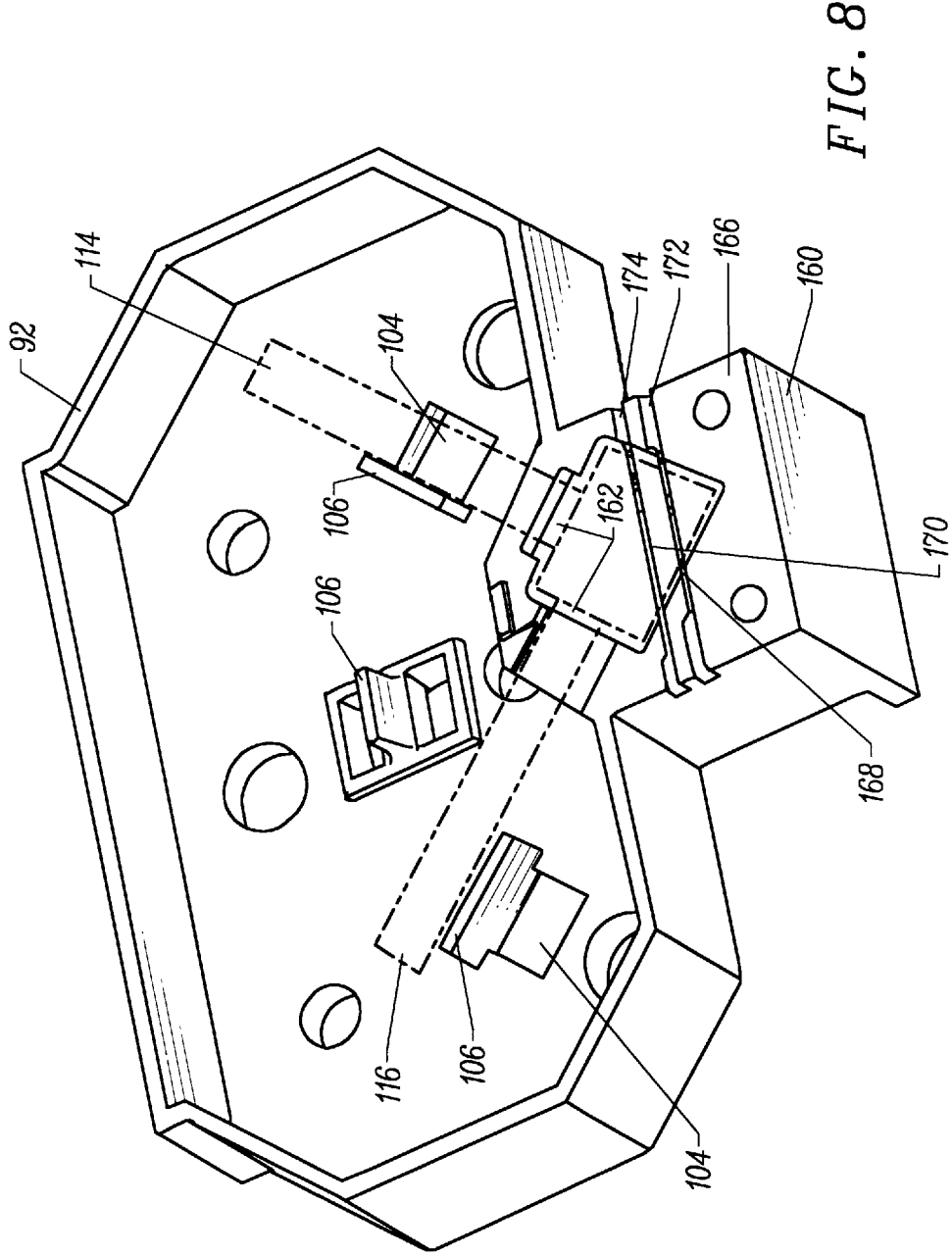
FIG. 8 is an isolated perspective view of the top side of the shield of the device in FIG. 4.

FIG. 8 is a view isolating the top side of the shield 92 and more specifically illustrates that the shield 92 is integrally formed with a base 160 which partially supports the assay strips 114, 116 at the ends proximal 162 to the inlet port as seen in FIG. 5. When the shield and the optics assembly 90 are assembled, the base 160 nests into the cut-away portion 164 of the optics assembly 90 as seen in FIG. 6. As seen in FIGS. 6 and 8, the top surface 166 of the base is approximately flush with the top face 108 of the optics assembly, providing uniform support across the length of the assay strips 114, 116.

As previously disclosed herein, the automatic start feature of the present invention is also illustrated in FIG. 8. The base 160 includes two channels 168 and 170 spaced in parallel across the top surface 166 of the base. The channels 168 and 170 are positioned to contact the sample upon its delivery through the inlet port either instantaneously or immediately downstream from the inlet port. Each channel 168, 170 is sized to accommodate an electrode 172, 174 respectively therein. Preferably, the diameter of each electrode is about 0.5 mm. The electrodes 172, 174 connect to a control circuit which causes a transition from a inactive or dormant state to an active state.

In the inactive state, very little power is consumed by the device 60. The microprocessor 42 is supplied only enough power required to maintain the volatile random access memory. The self-powering, automatic start feature allows the microprocessor in the inactive state to consume preferably less than about 5 $\mu$AH, more preferably less than about 1 $\mu$AH to 2 $\mu$AH, and most preferably about 0.1 $\mu$AH. The automatic start feature of the present invention changes the state of the processor from "stop" to "idle", or directly to a fully "active" state. The number of operational states of the particular microprocessor is easily accommodated by the automatic start feature.

In the active state, the device 60 becomes operational as the result of introducing the sample and wetting the pair of electrodes 172, 174. Thus, the automatic start feature of the present invention eliminates the need for a manual switch, or an on/off control that consumes a significant amount of power in the inactive state that will otherwise be needed later for operation of the device. The automatic start feature also provides a relatively precise starting time for the assay which is uniform regardless of the individual device. Manual switches or other means activated by the operator can not provide this accuracy. The precise starting time prevents wasting power caused by activating the microprocessor prematurely.

With the present invention, one skilled in the art can incorporate a battery in the device of the appropriate size taking into account the power consumption of the particular microprocessor, other than the examples herein, to provide the desired shorter or longer shelf-life.

Figure 9:
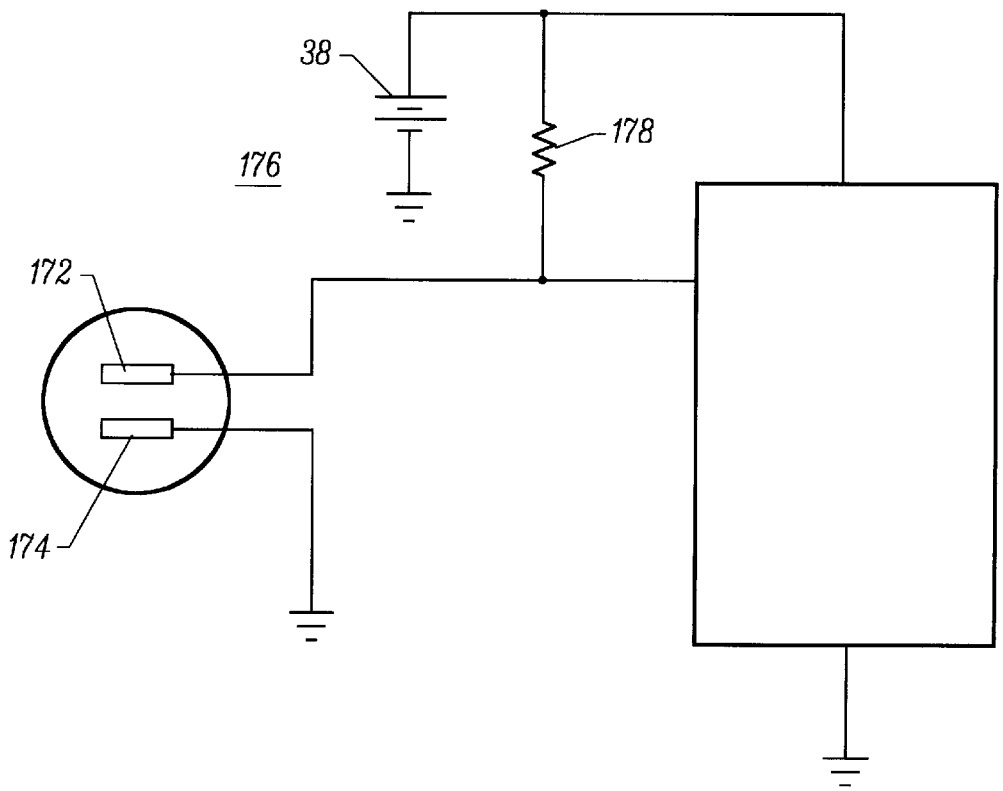
FIG. 9 is a schematic circuit configuration for one embodiment of the automatic start utilized by the present invention.

FIG. 9 illustrates the electrodes 172, 174 and a control circuit 176 of the automatic start feature in more detail. The electrodes 172, 174 are connected to the input of a control circuit that will respond to a change in potential between them. Electrode 174 is preferably a copper wire which is connected to ground and exhibits a zero voltage potential. Electrode 172 is preferably a zinc clad copper wire which connects to a power supply 38 through a resistor 178 and also to the processor 42. The power supply 38 also connects to the processor 42. When the device is in the dormant state, the potential exhibited at the electrode 172 reflects the potential of the battery which in this preferred embodiment is about +3v. After the sample is introduced to the device, the potential exhibited at the electrode 172 reverses polarity to −0.7v. The value of the resistor 178 for the preferred embodiment is about 2.2 Mohm.

The electrodes are made of dissimilar metals that create an electric potential between them when exposed to the sample. In the dormant or dry state, a potential of opposite polarity is applied to the electrodes through a resistor. Preferably, copper and zinc-clad copper wires are used as the electrodes. However, tin and silver are suitable and other metals which provide the needed potential and are easily incorporated into the manufacturing process can be used with the present invention.

In order to assure a shelf life of at least two years for the preferred embodiment illustrated in FIGS. 4 and 9, two A76 batteries having a capacity of 150 m AH are used. The control circuit consumes about 0.1 $\mu$AH at room temperature. This provides for adequate power for the device 60 in the operational state which consumes about 100 $\mu$a for about three minutes to complete the test.

Referring to FIG. 4, another feature of the present invention is illustrated in the manner that the quantitative assay results are displayed. In this preferred embodiment, an LCD 270 having a 3½ digit display capability is integrally mounted through the exterior surface 68 of the cover and is electrically connected to the processor. Each digit of the LCD 270, or fraction thereof, can be considered a separate screen for displaying pertinent information.

In the assay example illustrated, three different types of assay result information are printed along side the LCD 270 on the exterior surface 68 of the cover for HDL cholesterol, LDL cholesterol, and total cholesterol. When each assay result is displayed, a first component of the corresponding digital output displays a numerical output in a first screen 272. Simultaneously, a second component of the corresponding digital output displays a character in a second screen 274 indicating the identity of the assay result by pointing to the appropriate marking on the exterior surface of the cover. The simultaneous display of the identity and amount of one of the selected analytes, HDL cholesterol, remains for a predetermined period of time controlled by the processor. Upon expiration of the predetermined time period, the identity and amount of another one of the selected analytes, in this example LDL cholesterol, is displayed. This procedure is repeated for the total cholesterol result to complete a cycle. The cycle begins again by displaying the information for the first analyte, HDL cholesterol.

During the cycling of the display, the assay results can be updated by the processor. As previously discussed, other messages can be displayed by the LCD at various times during the cycle of the assay results. It is suitable to provide larger LCDs to display the assay results of all the analytes simultaneously. However, the added cost is commercially undesirable, particularly in a disposable device. It is also suitable to have the identity of the assay results displayed by the LCD 270 instead of printing a mark on the cover 64.

As previously discussed, the diagnostic device 60 can be of any convenient size with the optimal dimensions determined by several factors including convenience of use to the consumer. Preferably, the device 60 has a volume range of about 5 cm$^3$ to about 500 cm$^3$. More preferably, the volume of the device 60 is in the range of about 20 cm$^3$ to about 50 cm$^3$.

In the operation of one of the preferred embodiments of the present invention, the presence of one or more selected analytes in a sample is determined by reacting the sample, within the housing of a disposable device, with a reagent corresponding to the selected analyte to yield a physically detectable change which correlates with the amount of the selected analyte in the sample. Subsequently, the physically detectable change is calibrated using the assay calibration information previously described and transformed to a numerical output. The assay calibration information is uniquely characteristic to the specific reagent in the housing and to the physically detectable change for each selected analyte.

The term specific reagent refers to the reagent contained in the individual device housing. The chemistry (i.e. manufacturing lot number, etc.) of the specific reagent is known when the housing, interior components, and reagent are manufactured. As a result, the present invention can use assay calibration information that is unique to the specific reagent. Similarly, the assay calibration information can include specific, individual information on each component used in manufacturing the individual assay device. Preferably, the device is manufactured with the assay calibration information stored in the processor within the housing and all of the components sealed in the housing.

The assay calibration information can be used to determine the accuracy of the assay by measuring an electrical signal produced in response to the physically detectable change with a pre-determined range for the electrical signal. The physically detectable change can also be calibrated to a reference standard contained in or calculated using the assay calibration information. The assay results can also be adjusted to the ambient temperature of the device housing using the calibration information. The assay calibration information can be compared with the display output to determine the accuracy of the assay by including a pre-determined range for the display output in the information. Another method of determining the accuracy of the assay is to time the presence of the sample and compare the time required to achieve the assay result to the calibration information which can include a pre-determined range for that parameter.

Preferably, the quantitative assay results are displayed for each selected analyte in the sample by simultaneously displaying the identity and amount of one of the selected analytes for a predetermined period of time. Upon expiration of the predetermined time period the identity and amount of another one of the selected analytes is displayed. This procedure is repeated for each of the analytes to complete a cycle. The cycle begins again by displaying the information for the first analyte.

Preferably, the operation of the device begins automatically by sensing the introduction of the sample to the housing and generating a signal to activate the device. One of the preferred methods of sensing the introduction of the sample to the device includes creating a potential between a plurality of electrodes and changing the electrical potential between the electrodes upon contacting the sample with the electrodes. As discussed above, at least one electrode is connected to a power supply and the device. The other electrode is connected to a ground to create an electrical potential therebetween which changes upon contact of the electrodes with the sample. The voltage transition is then signaled to the device.

Having generally described the present invention, a further understanding can be obtained by reference to the following specific examples, which are provided herein for purposes of illustration only and are not intended to be limiting of the present invention.

EXAMPLE 1

Figure 10:
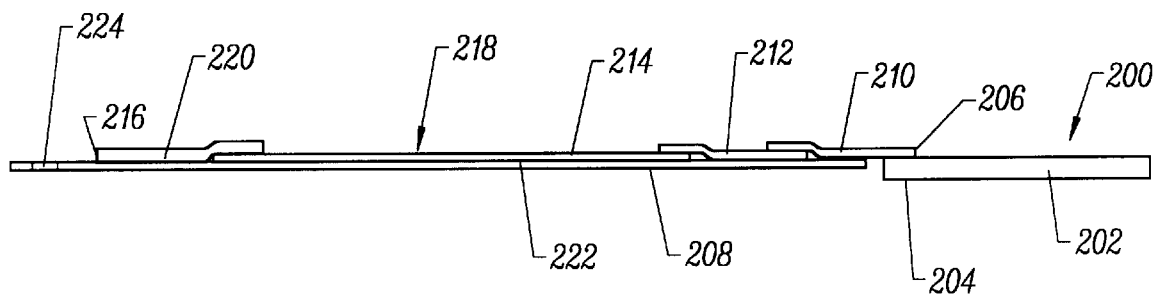
FIG. 10 is a side view of one embodiment of an assay strip suitable for use in an NTx assay.
Figure 11:
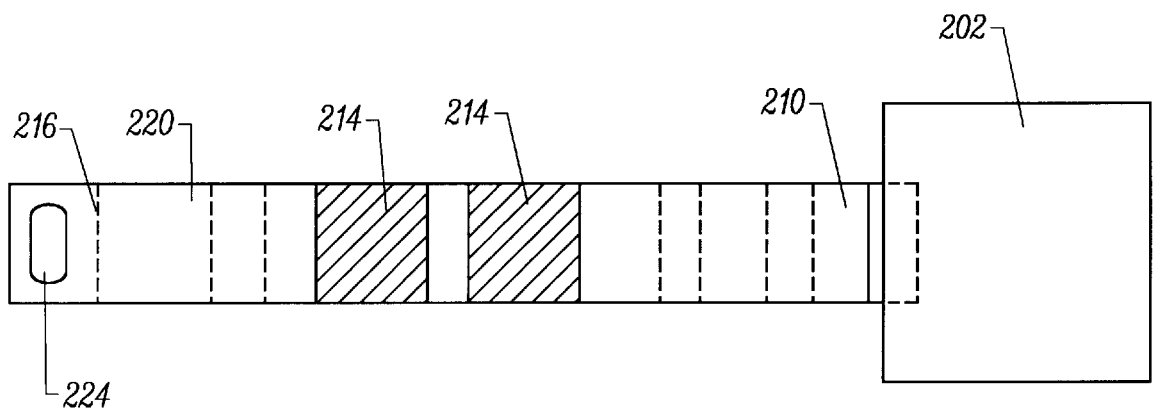
FIG. 11 is a top plan view of the assay strip in FIG. 10.

FIGS. 10 and 11 illustrate a laminated strip layout 200 for an NTx assay which is suitable for use in the preferred embodiment of the diagnostic device 60 described above. The strip layout 200 includes a sample distribution pad 202 for receiving the sample through the inlet port (not shown) to the top side 204 of the sample distribution pad 202 at the proximal end 206 of the strip. The distribution pad 202 which is made of material from CytoSep No. 1662 having approximately square dimensions of about 7 mm with a thickness of about 0.023 mm. The sample distribution pad 202 attaches to and is in fluid communication with two assay strips like 114 and 116 previously illustrated in FIG. 4. One of these strips is represented in FIGS. 10 and 11 as assay strip 208 which is made of multiple components.

The sample flows to a sample treatment pad 210 and subsequently to a conjugate pad 212. Both pads 210 and 212 are made of a material from Accuwik No. 14–20 and each is about 4 mm long and 3 mm wide with a thickness of about 0.00945 inches. The conjugate pad 212 contains a diffusively immobilized conjugate of blue polystyrene microparticles with a mouse monoclonal antibody to NTx and is in fluid communication with a reagent strip 214 made of nitrocellulose material from Schleicher & Schuell P/N AE98 having a size of about 12.4 mm long and about 3 mm wide with a thickness of about 0.004685 inches. The reagent strip 214 contains the chemical reagents for performing the assay to produce a physically detectable change on the underside 218 of the strip to be measured by the detector previously described. There are two zones of non-diffusively immobilized materials on reagent strip 214: the first zone containing NTx antigen and the second zone containing goat antibody to mouse IgG. The reagent strip 214 allows the treated sample to flow quickly towards the distal end 216 of the strip where excess sample is collected by an end pad 220. As seen in FIG. 6, the top face 108 of the optics assembly provides an indentation 84 for each assay strip to accommodate the end pad 220. The end pad is made of material from Schleicher & Schuell P/N GB 002 having dimensions of about 3 mm wide and about 4 mm long with a thickness of about 0.019 inches.

The pads 210, 212, and 214 are supported and attached to a backing material 222 which is made of poly(ethylene terephthalate) plastic from Adhesives Research with an adhesive P/N 8565. The backing material is about 22.5 mm long and about 3 mm wide with a thickness of about 0.01 mm. The distal end 216 of the strip includes an index hole 224 in the backing material 218 which engages the pin 78 for positioning the strip 208 as seen in FIG. 6.

EXAMPLE 2

Figure 12:
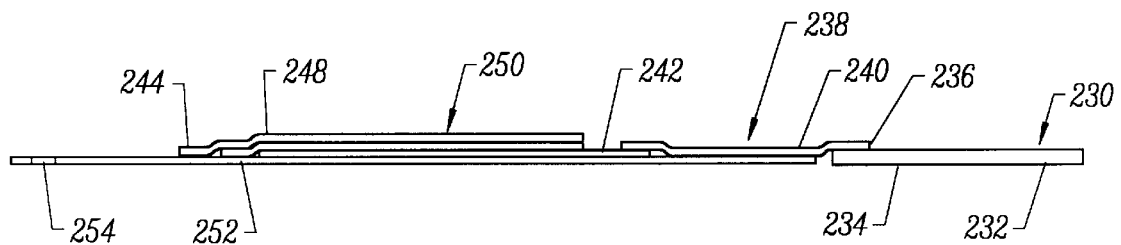
FIG. 12 is a side view of one embodiment of an assay strip suitable for use in a general chemistry assay.
Figure 13:
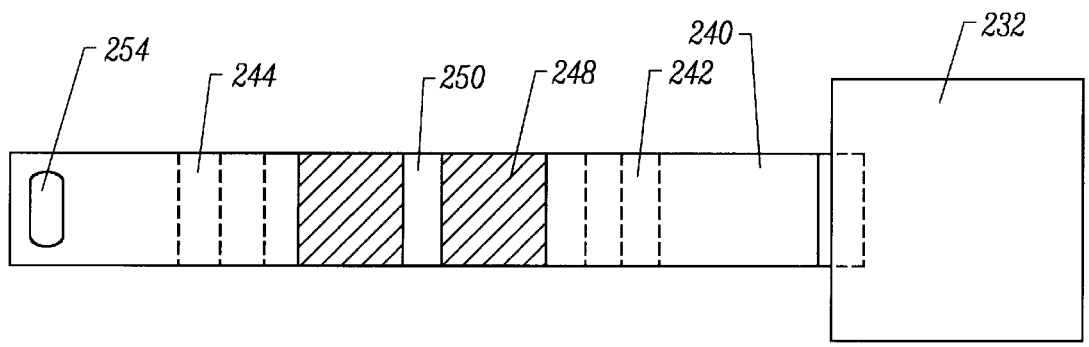
FIG. 13 is a top plan view of the assay strip in FIG. 12.

FIGS. 12 and 13 illustrate a laminated strip layout 230 for a general chemistry assay which is suitable for use in the preferred embodiment of the diagnostic device 60 described above. The strip layout 230 includes a sample distribution pad 232 for receiving the sample through the inlet port (not shown) on the topside 234 of the pad 232 at the proximal end 236 of the strip 238. The distribution pad 232 is made of material from CytoSep No. 1662 having approximately square dimensions of about 7 mm with a thickness of about 0.023 inches. The sample distribution pad 232 attaches to and is in fluid communication with two assay strips like 114 and 116 previously illustrated in FIG. 4.

The sample flows from the distribution pad 232 to a sample treatment pad 240 which is made of a material from Pall Biosupport Accuwik No. 14–20, is about 7 mm long and 3 mm wide with a thickness of about 0.00945 inches. The sample treatment pad 240 is in fluid communication with a transport matrix 242 made of polyester substrate from Tetko P/N 7-2F777 BM having a size of about 11 mm long and about 3 mm wide with a thickness of about 0.00846 inches. The transport matrix 242 allows the treated sample to flow quickly towards the distal end 244 of the strip. Substantially overlapping the transport matrix 242 is a spreading layer 246 which assists in spreading the treated sample across the length of the strip. A reagent layer 248 substantially overlaps the spreading layer 246 and contains the chemical reagents for performing the assay to produce a physically detectable change on the top surface 250 of the reagent layer which is measured by the detector previously described. The reagent layer contains the dried chemical components needed to measure creatinine in the sample: the solution for dipping the indicator included 0.5% w/v sucrose, 1.0% w/v polyvinyl-pyrrolidone (avg. mw. about 40,000), 5% v/v surfactant 10G (p-isononylphenoxypoly(glycidol)) and 75 mg/ml bis(4-(N-(3'-sulfo-n-propyl)-N-n-propyl)amino-2,6-dimethylphenyl)methane,disodium salt; the enzyme solution used for dipping the reagent layer included 1000 u/ml horse radish peroxidase (EC 1.11.17), 500 u/ml sarcosive oxidase (EC 1.5.3.1), 5000 u/ml creatinine amidinohydrolase (EC 3.5.3.3), 1200 u/ml creatinine amidohydrolase (EC 3.5.2.10) (all from the Toyobo Company), 1% w/v poly(vinyl alcohol) (avg. mw. about 70,000), 1% v/v Triton X-100

(t-octylphenoxypolyethoxyethanol), 1% w/v sucrose, 5 mg/ml Bovine Serum Albumin, and 50 mM buffer 3-(N-morpholino)-2-hydroxypropanesulfonic acid, sodium salt, pH 7.5.

The sample treatment pad 240 and the transport matrix 242 are supported and attached to a backing material 252 which is made of poly(ethylene terephthalate) plastic from Adhesives Research with an adhesive P/N 8565. The backing material is about 22.5 mm long and about 3 mm wide with a thickness of about 0.01 mm. The distal end 244 of the strip includes an index hole 254 in the backing material 252 which engages the pin 78 for positioning the strip 238 as seen in FIG. 5.

Numerous modifications and variations of the present invention are possible in light of the above teachings. It is therefore to be understood that within the scope of the appended claims, the invention may be practiced otherwise than as specifically described herein.

What is claimed is:

1. An assay device for determining the presence of one or more selected analytes in a sample, the device comprising:
   a housing having an exterior surface and defining an interior area;
   sample receptor means for receiving a sample, the sample receptor means being located on the exterior surface of the housing;
   sample treatment means for reacting the sample with a reagent to yield a physically detectable change which correlates with the amount of selected analyte in the sample, the sample treatment means being located within the housing and in fluid communication with the sample receptor means;
   detector means for responding to the physically detectable change and producing an electrical signal which correlates to the amount of selected analyte in the sample, the detector means being located within the housing and in electrical or optical communication with the sample treatment means;
   processing means for storing assay calibration information, the assay calibration information being uniquely characteristic to the specific reagent and physically detectable change of the sample treatment means and to the specific detector means of the individual assay device, the processing means further calibrating the sample treatment means and the detector means using the stored assay calibration information, and the processing means further converting the electrical signal to a digital output, the processing means being located within the housing and connected to the detector means;
   starting means for automatically activating the processing means and detector means upon the application of the sample to the device, the starting means being located within the housing and connecting to the processing means; and
   display means for visually displaying the digital output external to the housing, the display means being connected to the processing means.

2. The assay device of claim 1 wherein the starting means includes a sensor positioned within the housing and in fluid communication with the sample, the sensor contacts the sample prior to the physically detectable change from reacting the sample with the reagent being produced, the sensor generates a signal upon contact with the sample, and the signal is transmitted to the processing means.

3. The assay device of claim 2 wherein the sensor includes two electrodes spaced apart from one another and in fluid communication with the sample, at least one of the electrodes being electrically connected to the processing means.

4. The assay device of claim 3 wherein the starting means further includes electrically connecting one electrode to a power supply and the processing means, the other electrode is electrically connected to a ground, each of the electrodes is made of a different metal so that an electrical potential is created therebetween upon contact of the electrodes with the sample to create a voltage transition which is signaled to the processing means.

5. The assay device of claim 1 wherein the starting means is positioned within the sample receptor means in fluid communication with the sample.

6. The assay device of claim 1 wherein the processing means further times the period from activation by the starting means to stabilization of the physically detectable change, and compares the timed period to the stored assay calibration information to determine the accuracy of an assay performed with the device, the stored assay calibration information including a pre-determined range for the timed period.

7. The assay device of claim 1 wherein the detector means further includes producing a reference electrical signal upon activation by the starting means which correlates to the sample treatment means prior to contact with the sample; and the processing means further includes comparing the reference electrical signal to the electrical signal received from the detector means after stabilization of the physically detectable change.

8. A multi-assay device for determining the presence of a plurality of selected analytes in a sample, the multi-assay device comprising:
   a housing having an exterior surface and defining an interior area;
   sample receptor means for receiving a sample, the sample receptor means being located on the exterior surface of the housing;
   sample treatment means for reacting the sample with a plurality of reagents corresponding to the plurality of selected analytes to yield physically detectable changes which each correlate with the amount of one of the selected analytes in the sample, the sample treatment means being located within the housing and in fluid communication with the sample receptor means;
   detector means for responding to the physically detectable changes and producing electrical signals which each correlate to the amount of one of the selected analytes in the sample, the detector means being located within the housing and in electrical or optical communication with the sample treatment means;
   processing means for storing assay calibration information, the assay calibration information being uniquely characteristic to the specific reagent and physically detectable change of the sample treatment means and to the specific detector means of the individual multi-assay device, the processing means further calibrating the sample treatment means and the detector means using the stored assay calibration information, and the processing means further converting each electrical signal to a digital output corresponding to each selected analyte, the processing means being located within the housing and connected to the detector means; and
   display means for externally displaying each digital output corresponding to one of the selected analytes, each digital output having assay result information of one of the selected analytes, the display means being connected to the processing means.

9. The multi-assay device of claim 8 wherein the display means further includes a plurality of screens, and for each digital output a first of the plurality of screens visually displays a first component of the digital output having the identity of a selected analyte, and a second of the plurality of screens visually displays the amount of the corresponding selected analyte.

10. The multi-assay device of claim 9 wherein the display means further includes simultaneously displaying the identity and amount of one selected analyte corresponding to one digital output, the processor means cycling each digital output to the display means for a predetermined period of time.

11. An assay device for providing quantitative measurement of one or more selected analytes in a sample using reflected optical radiation, the device comprising:
   a housing having an exterior surface and sealing an interior area;
   a receptor configured to receive a sample containing an analyte, the receptor being located on the exterior surface of the housing;
   at least one assay strip for reacting the sample with a self-contained reagent to yield a physically detectable change in at least one sampling area on each assay strip which correlates with the amount of selected analyte in the sample, each assay strip being in fluid communication with the receptor;
   a reflectometer having an optical radiation source, a detector configured to quantitatively detect optical radiation, and an optics assembly configured to direct illumination from the optical radiation source to each sampling area on the at least one assay strip and to direct radiation diffusely reflected from each sampling area to the detector, the detector producing an electrical signal which correlates to the amount of the selected analyte in the sample;
   a processor configured to store assay calibration information, the assay calibration information being uniquely characteristic to the specific self-contained reagent and physically detectable change within each sampling area and to the specific reflectometer of the individual assay device, the processor further configured to calibrate each sampling area and the reflectometer using the stored assay calibration information, and the processor further configured to convert each electrical signal to a digital output, the processor being sealed within the housing and connected to the reflectometer;
   a starter configured to automatically activate the processor and reflectometer upon the application of the sample to the device, the starter being located within the housing and connecting to the processor; and
   a display configured to visually display each digital output external to the housing, the display being connected to the processor.

12. The assay device of claim 11 wherein each assay strip includes at least two sampling areas, the processor further configured to calibrate each assay strip by summing the electrical signal from each sampling area to one another and comparing the sum to the electrical signal of each sampling area or to the stored assay calibration information.

13. The assay device of claim 11 wherein the display is further configured to individually display the digital output from each assay strip in a predetermined cycle.

14. The assay device of claim 11 wherein the device further includes a filter configured to remove contaminants from the sample, the filter is in fluid communication with each assay strip prior to a sampling area.

15. A method of determining the presence of one or more selected analytes in a sample using a disposable housing, the method comprising the steps of:
   reacting a sample within the housing with a reagent corresponding to one or more of the selected analytes to yield a physically detectable change which correlates with the amount of the selected analyte in the sample;
   calibrating the physically detectable change using assay calibration information uniquely characteristic to the specific reagent in the housing and to the physically detectable change for the selected analyte to determine the amount of the selected analyte; and
   displaying the amount of the selected analyte.

16. The method of claim 15 wherein, after the reacting step, the method further includes the steps of:
   producing an electrical signal which correlates with the amount of the corresponding selected analyte in the sample;
   converting the electrical signal to a digital output;
   and the displaying step further includes displaying the digital output.

17. The method of claim 16 wherein the method further includes the step of comparing the calibration information with the electrical signal to determine the accuracy of the method, the calibration information including a pre-determined range for the electrical signal.

18. The method of claim 15 wherein the method further includes the step of storing the assay calibration information within the housing prior to the reacting step.

19. The method of claim 15 wherein the method further includes the step of sealing the housing prior to the reacting step.

20. The method of claim 15 wherein, prior to the calibrating step, the method further includes the step of:
   reacting at least a portion of a reaction mixture of the sample and the reagent with a second reagent to produce a reaction product with a physically detectable label which correlates with the amount of selected analyte in the sample.

21. The method of claim 15 wherein the method further includes the step of calibrating the physically detectable change to a reference standard.

22. The method of claim 15 wherein the method further includes the step of adjusting the determined amount of the selected analyte to the ambient temperature of the housing using the calibration information.

23. The method of claim 15 wherein the method further includes the step of comparing the calibration information with the display of the amount of the selected analyte to determine the accuracy of the method, the calibration information including a pre-determined range for the display of the amount of the selected analyte.

24. The method of claim 15 wherein the method further includes the steps of measuring a length of time the sample reacts with the reagent and comparing the timed reaction of the sample to the calibration, information to determine the accuracy of the method, the calibration information including a pre-determined range for the timed reaction of the sample.

25. The method of claim 15 wherein the method further includes the step of starting the method automatically upon introduction of the sample to the housing.

26. The method of claim 15 wherein the method further includes the step of performing the reacting and calibrating steps for each of a plurality of analytes to be determined in the sample; and the displaying step further includes simultaneously displaying the determined amount of one selected analyte and cycling the display of assay results of each selected analyte for a predetermined period of time.

27. A method of automatically starting a diagnostic device and of determining the presence of one or more selected analytes in a sample, the method comprising the steps of:

sensing the introduction of a sample to a single-use, disposable device and generating a signal to activate the device; and reacting a self-contained reagent located within the device with one or more selected analytes in the sample to yield a physically detectable change which correlates with assay calibration information stored within the device which is uniquely characteristic to the specific self-contained reagent and physically detectable change.

28. The method of claim 27 wherein the sensing step includes creating an electrical potential between a plurality of electrodes and changing the electrical potential between the electrodes upon contacting the sample with the electrodes.

29. The method of claim 28 wherein the sensing step further includes the steps of:

connecting at least one electrode to a power supply and the device;

connecting at least one other electrode to a ground to create an electrical potential therebetween which changes upon contact of the electrodes with the sample; and signaling the changing electrical potential to the device.

* * * * *